(12) United States Patent
Raptis et al.

(10) Patent No.: US 11,186,532 B1
(45) Date of Patent: Nov. 30, 2021

(54) DINUCLEAR COPPER CATALYST FOR THE OXIDATION/OXYGENATION OF HYDROCARBONS

(71) Applicants: Raphael G. Raptis, Coral Gables, FL (US); Logesh Mathivathanan, Tamil Nadu (IN)

(72) Inventors: Raphael G. Raptis, Coral Gables, FL (US); Logesh Mathivathanan, Tamil Nadu (IN)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/159,519

(22) Filed: Jan. 27, 2021

(51) Int. Cl.
| | | |
|---|---|---|
| *C07C 37/60* | (2006.01) |
| *B01J 31/18* | (2006.01) |
| *C07C 45/28* | (2006.01) |
| *C07C 5/367* | (2006.01) |
| *C07C 29/48* | (2006.01) |

(52) U.S. Cl.
CPC .......... *C07C 37/60* (2013.01); *B01J 31/1815* (2013.01); *C07C 5/367* (2013.01); *C07C 29/48* (2013.01); *C07C 45/28* (2013.01); *B01J 2231/46* (2013.01); *B01J 2231/763* (2013.01); *B01J 2231/766* (2013.01); *B01J 2531/004* (2013.01); *B01J 2531/0208* (2013.01); *B01J 2531/16* (2013.01); *C07C 2531/22* (2013.01)

(58) Field of Classification Search
None
See application file for complete search history.

(56) References Cited

U.S. PATENT DOCUMENTS 9,416,080 B2    8/2016    Warren et al.

OTHER PUBLICATIONS

Tsuji et al. (Angew. Chem. Int. Ed., 2017, 36, 7779-7782 (Year: 2017).*
Herrera, S., "Bio-Inspired Dinuclear Copper Oxygenation Catalysts: Synthesis, Characterization, and Reactivity Studies." Undergraduate Research at FIU (URFIU) Conference, 2016, poster. Department of Chemistry and Biochemistry, Florida International University, Miami, FL, USA.
Feng, X., et al., "Rational Construction of an Artificial Binuclear Copper Monooxygenase in a Metal-Organic Framework." Journal of the American Chemical Society, 2021,143: 1107-1118.
Herrera, S., "Bio-Inspired Dinuclear Copper Oxygenation Catalysts: Synthesis, Characterization, and Reactivity Studies." Undergraduate Research at FIU (URFIU) Conference, 2016, Abstract, (retrieved from the internet Mar. 29, 2021: https://digitalcommons.fiu.edu/cgi/viewcontent.cgi?article=1188&context=fiu-undergraduate-research-conference).
Holm, R.H., "Metal-Centered Oxygen Atom Transfer Reactions." Chem. Rev., 1987, 87: 1401-1449.
Mathivathanan, L., et al., "Evaluation of oxygen-transfer properties of dinuclear copper pyrazolato complexes." Abstracts of Papers of the American Chemical Society, 2019, vol. 257, Abstract, 1155 16th St, NW, Washington, DC 20036 USA: Amer Chemical Soc.
Mathivathanan, L., et al., "Evaluation of oxygen-transfer properties of dinuclear copper pyrazolato complexes." Abstracts of Papers of the American Chemical Society, 2019, Presentation, 1155 16th St, NE, Washington, DC 20036 USA: Amer Chemical Soc.
Paul, M., et al., "Substrate Diversity in Oxygenation Reactions Catalyzed by a Bis(µ-oxo) Copper Complex." Chemistry-A European Journal, 2020, 26: 7556-7562.

* cited by examiner

*Primary Examiner* — Yun Qian
(74) *Attorney, Agent, or Firm* — Saliwanchik, Lloyd & Eisenschenk (57) ABSTRACT

The subject invention provides synthetic compounds, and compound complexes having catalytic activities towards oxidation or oxygenation, and/or dehydrogenation of various substrates comprising C—H bonds. The catalysts of the subject invention comprise a dinuclear Cu(I)/Cu(II) center that can convert between a resting state and a reactive species. The subject invention also provides methods of using such catalysts for the oxidation of substrates comprising C—H bonds, e.g., hydrocarbons, to synthesize chemicals for use as pharmaceuticals and industrial feedstock.

20 Claims, 2 Drawing Sheets
(2 of 2 Drawing Sheet(s) Filed in Color)

DINUCLEAR COPPER CATALYST FOR THE OXIDATION/OXYGENATION OF HYDROCARBONS

BACKGROUND OF THE INVENTION

Copper plays a wide variety of roles in, for example, electron transfer (ET), $O_2$ binding, activation and reduction, and substrate activation due to its accessible I/II redox couple and bioavailability. One property of Cu is the existence in either a reduced, $Cu^+$, or oxidized, $Cu^{2+}$, state. Since $Cu^+$ has an affinity for thiol and thioether groups while $Cu^{2+}$ exhibits preferred coordination to oxygen or imidazole nitrogen groups, such metal ion can participate in a wide spectrum of interactions with proteins to drive diverse structures and biochemical reactions.

Metalloproteins are important proteins that include a metal center, such as Fe, Ca, Cu or Zn, and a protein structure, typically composed of elements such as carbon, nitrogen, oxygen, hydrogen and sulfur, surrounding the metal center. The metal center may contain one or more metal atoms. Dinuclear copper assemblies are encountered in the active centers of various metalloproteins, such as hemocyanin, tyrosinase, catechol oxidase, laccase and particulate methane monooxygenase (pMMO).

The dinuclear copper center can catalyze intricate chemical reactions of biological importance. For example, pMMO catalyzes the conversion of methane to methanol. The role of the protein backbone in these metalloproteins is to hold the two Cu-centers together in a manner allowing them to reach close proximity upon two-electron oxidation of the Cu(I) rest state to the Cu(II) catalytically active form. For example, in catechol oxidase, the distance between two Cu(I) is 4.4 Å while the distance between two Cu(II) is 2.5 Å.

There has been an interest to produce synthetic catalysts that can bring the two copper centers together to mimic the functionality of those Cu-containing proteins. Redox and magnetic properties are also major research foci of dicopper chemistry. Thus, it is desired to develop and/or synthesize copper-containing complexes for catalyzing crucial conversions of biological or industrial importance, by facilitating various C—H activation reactions, e.g., oxidizing $sp^3$-hybridized C—H bonds.

Further, the oxidation/oxygenation of hydrocarbons has been recognized to play a role in infectious and neurodegenerative diseases. Thus, there is also a need to develop and/or synthesize copper-containing catalysts for producing specific chemicals for pharmaceutical and industrial applications.

BRIEF SUMMARY OF THE INVENTION

The subject invention provides synthetic copper-containing complexes having catalytic activities towards oxidation or oxygenation, and/or dehydrogenation of various substrates comprising C—H bonds, and compositions comprising such copper-containing complexes. The copper-containing complexes comprise one or more copper atoms that can convert between a resting state (a reduced oxidation state) and a catalytically-active state (oxidized state), thereby recycling the reactive species for the subsequent catalytic cycles.

In one embodiment, the substrates comprising C—H bonds are hydrocarbons. In a further embodiment, the hydrocarbons are selected from straight, branched, cyclic, saturated or unsaturated alkanes, alkenes, alkynes, heterocycles, aromatics and polymeric compounds.

In one embodiment, the subject invention provides a copper-containing catalyst comprising a dinuclear copper complex that comprises a copper-containing compound having a bi-copper center joined by bidentate or multidentate ligands, and optionally, the dinuclear copper complex comprising a stabilizing counter ion. In a further embodiment, the bi-copper center comprises a μ-OH that can form a hydrogen bond with the stabilizing counter ion. The bidentate or multidentate ligands and the stabilizing counter ion may be the same or different.

The dinuclear copper complex shows catalytic activity towards oxidation or oxygenation of substrates comprising at least one C—H bond, e.g., hydrocarbons, and cycle between a Cu(II)—OH—Cu(II) form and a Cu(I)-Cu(I) resting state, as follows: the Cu(I)-Cu(I) resting state of the dinuclear copper complex is oxidized by, for example, atmospheric oxygen, or other reactive species to form a Cu(II)—OH—Cu(II) species. The latter reacts with substrates comprising at least one C—H bond, e.g., hydrocarbons, either dehydrogenating them with formation of $H_2O$, or oxygenating them by adding its O-atom to the substrate. Upon reaction with the substrates, e.g., hydrocarbons, the complex returns to the Cu(I)-Cu(I) state, closing the catalytic cycle. While the copper complex is in its rest Cu(I)-Cu(I) state, the H-atom of Cu(II)—OH—Cu(II) is bound to the counter ion (neutralizing its charge), from where it is shuttled back to the complex upon re-oxidation.

In one embodiment, the subject invention provides a dinuclear copper catalyst comprising a dinuclear copper complex and a stabilizing counter ion, wherein the dinuclear copper complex cycles between a resting dinuclear Cu(I) complex and a catalytic dinuclear Cu(II) complex, the catalytic dinuclear Cu(II) complex comprising a Cu(II)—OH—Cu(II) center.

Advantageously, the synthesis of the dinuclear copper catalyst of the subject invention is cost-effective, which makes the production of specific chemicals using such dinuclear copper catalyst inexpensive. Also, value may be added to low grade hydrocarbons that can be used as substrates of the dinuclear copper catalyst.

In one embodiment, the resting dinuclear Cu(I) complex has a general structure of the formula (A):

wherein represents a peripheral chelating ligand substitution, preferably, is and wherein $R_1$, $R_3$, $R_4$, $R_5$, $R_6$, $R_3'$, $R_4'$, $R_5'$, $R_6'$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, —COOH, —NO$_2$, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, acyl, carboxyalkyl, halogen, amino, substituted amino, hydroxyl, hydroxylalkyl, and substituted hydroxylalkyl.

In one embodiment, the catalytic dinuclear Cu(II) complex has a general structure of the formula (B):

wherein represents a peripheral chelating ligand substitution, preferably, is and wherein $R_1$, $R_3$, $R_4$, $R_5$, $R_6$, $R_3'$, $R_4'$, $R_5'$, $R_6'$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, —COOH, —NO$_2$, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, acyl, carboxyalkyl, halogen, amino, substituted amino, hydroxyl, hydroxylalkyl, and substituted hydroxylalkyl.

In one embodiment, the dinuclear copper catalyst comprises a stabilizing free ligand as counterion, whose ionic form has a general structure of that can form a hydrogen bond with the μ-OH of the dinuclear Cu(II) complex, while the neutral form of the free ligand has a general structure of, wherein $R_1$, $R_2'''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, —COOH, —$NO_2$, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, acyl, carboxyalkyl, halogen, amino, substituted amino, hydroxyl, hydroxylalkyl, and substituted hydroxylalkyl.

The subject invention further provides methods for using the dinuclear copper catalyst for the oxidation of substrates comprising C—H bonds, including dehydrogenation and oxygenation of substrates comprising C—H bonds.

In one embodiment, the subject invention provides a method for oxidizing or oxygenating a hydrocarbon comprising contacting, combining, and/or mixing the dinuclear copper catalyst of the subject invention with the hydrocarbon.

In one embodiment, the subject invention provides a method for forming an alcohol, an aldehyde, an alkene or an aromatic from a hydrocarbon, the method comprising contacting, combining, and/or mixing the hydrocarbon with the dinuclear copper catalyst of the subject invention. In a further embodiment, the alcohol is a primary alcohol, a secondary alcohol, or a tertiary alcohol.

In certain embodiments, the hydrocarbon is selected from alkanes, alkenes, alkynes, aromatics and polymeric compounds. In specific embodiments, the hydrocarbon is selected from dihydroanthracene (DHA), toluene, tetrahydrofuran (THF), 2,2,4-trimethylpentane, methylcyclohexane, methane, cyclopropane, cyclobutane, cyclopentane, cyclohexane and polyethylene.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

The subject invention provides synthetic copper-containing complexes having catalytic activities towards oxidation or oxygenation, and/or dehydrogenation of various substrates comprising C—H bonds. Such copper-containing complexes comprise one or more copper atoms that can convert between a resting state (a reduced oxidation state) and a catalytically-active state (oxidized state), thereby recycling the reactive species for subsequent catalytic cycles.

In one embodiment, the substrates comprising C—H bonds are hydrocarbons. In a further embodiment, the hydrocarbons are selected from straight, branched, cyclic, saturated or unsaturated alkanes, alkenes, alkynes, heterocycles, aromatics and polymeric compounds.

The subject invention provides compositions comprising the copper-containing complexes. The subject invention also provides methods for using such copper-containing complexes for the oxidation of substrates comprising C—H bonds, including dehydrogenation and oxygenation of substrates comprising C—H bonds. Upon reacting with substrates comprising C—H bonds, e.g., hydrocarbons, the cooper-containing complexes returns to the resting state, closing the catalytic cycle.

In one embodiment, the subject invention provides a copper-containing catalyst comprising a copper-containing compound having one or more copper centers complexed with one or more bidentate or multidentate ligands and, optionally, a stabilizing ligand or counter ion, wherein the copper centers comprise a μ-OH that forms a hydrogen bond with the stabilizing ligand or counter ion.

In a preferred embodiment, the copper-containing catalyst comprises a dinuclear copper complex comprising a copper-containing compound having a bi-copper center joined by bidentate or multidentate ligands and, optionally, a stabilizing ligand or counter ion, wherein the bi-copper center comprises a μ-OH that forms a hydrogen bond with the stabilizing ligand or counter ion. The bidentate or multidentate ligands and the stabilizing ligand or counter ion may be the same or different.

Definitions

As used herein, the term "hydrocarbon" refers to any molecule having carbon and hydrogen in any combination. "Hydrocarbon" includes straight-chain, branched, cyclic, saturated or unsaturated alkanes, alkenes, alkynes, heterocycles, aromatics and polymeric compounds.

The term "alkane" refers to any saturated hydrocarbon. "Alkane" may include straight-chain, branched, and cyclic alkanes (including monocyclic and polycyclic alkanes). The straight-chain or branched alkanes may have a general formula of $C_nH_{2n+2}$. The monocyclic alkanes may have a general formula of $C_nH_{2n}$. Examples include, but are not limited to, methane, ethane, propane, butane, pentane, hexane, heptane, octane, nonane, decane, undecane, dodecane, tridecane, tetradecane, pentadecane, hexadecane, heptadecane, octadecane, nonadecane, icosane, triacontane, cyclopropane, cyclobutane, cyclopentane, cyclohexane, cycloheptane, cyclooctane, and the like.

The term "alkene" refers to any hydrocarbon that contains one or more carbon-carbon double bonds. "Alkene" may include straight-chain, branched, and cyclic alkenes (including monocyclic and polycyclic alkenes). Examples include, but are not limited to, ethane, propene, butene, pentene, hexene, heptene, octene, nonene, decene, dodecene, propadiene, butadiene, pentadiene, hexadiene, octadiene, and the like.

The term "alkyne" refers to any hydrocarbon that contains one or more carbon-carbon triple bonds. "Alkyne" may include straight-chain, branched, and cyclic alkynes. Those with one triple bond have a general formula of $C_nH_{2n-2}$. Examples include, but are not limited to, ethyne, propyne, butyne, pentyne, hexyne, heptyne, octyne, nonyne, decyne, and the like.

The term "aromatic hydrocarbon," also known as arene, refers to any hydrocarbon that has at least one aromatic ring.

As used herein, "alkyl" means saturated monovalent radicals of at least one carbon atom or a branched saturated monovalent of at least three carbon atoms. It may include straight-chain alkyl groups, branched-chain alkyl groups, cycloalkyl (alicyclic) groups, alkyl substituted cycloalkyl groups, and cycloalkyl substituted alkyl groups. It may include hydrocarbon radicals of at least one carbon atom, which may be linear. Examples include, but are not limited to, methyl, ethyl, propyl, 2-propyl, n-butyl, iso-butyl, tert-butyl, pentyl, hexyl, and the like.

As used herein, "acyl" means a group —C(O)R where R includes, but is not limited to, hydrogen, alkyl or cycloalkyl, and heterocycloalkyl. Examples include, but are not limited to, formyl, acetyl, ethylcarbonyl, and the like. An aryl group may be substituted or unsubstituted.

As used herein, the terms "alkoxyl" or "alkoxy" refer to an alkyl group, as defined above, having an oxygen radical attached thereto. Examples include, but are not limited to, methoxy, ethoxy, propyloxy, tert-butoxy and the like.

As used herein, "carboxyalkyl" means a group —COOR where R includes, but is not limited to, hydrogen, alkyl or cycloalkyl, and heterocycloalkyl. Examples include, but are not limited to, carboxymethyl, carboxyethyl, carboxyphenyl, and the like. An alkyl or phenyl group may be substituted or unsubstituted.

As used herein, "alkylamino" means a radical —NHR or —NR$_2$ where each R is, independently, an alkyl group. Examples include, but are not limited to, methylamino, (1-methylethyl)amino, dimethyl amino, methylethylamino, di(1-methylethyl)amino, and the like. An alkylamino may be substituted or unsubstituted.

As used herein, "hydroxyalkyl" means an alkyl group substituted with one or more hydroxy groups. Representative examples include, but are not limited to, hydroxymethyl, 2-hydroxyethyl; 2-hydroxypropyl; 3-hydroxypropyl; 1-(hydroxymethyl)-2-methylpropyl; 2-hydroxybutyl; 3-hydroxybutyl; 4-hydroxybutyl; 2,3-dihydroxypropyl; 2-hydroxy-1-hydroxymethylethyl; 2,3-dihydroxybutyl; 3,4-dihydroxybutyl and 2-(hydroxymethyl)-3-hydroxy-propyl; preferably 2-hydroxyethyl; 2,3-dihydroxypropyl and 1-(hydroxymethyl) 2-hydroxyethyl. A hydroxyalkyl may be substituted or unsubstituted.

As used herein, "alkenyl" refers to a straight or branched hydrocarbon chain containing one or more double bonds. Although the present definition covers the occurrence of the term "alkenyl" where no numerical range is designated, the alkenyl group may have at least 2, 3, 4, 5, 6, 7, 8, 9, 10, 11, 12, 13, 14, 15, 16, 17, 18, 19, or 20 carbon atoms, or any number in between. For example, the alkenyl group may be designated as "$C_{2-4}$ alkenyl," "$C_{2-10}$ alkenyl," "$C_{2-20}$ alkenyl" or similar designations. By way of example only, "$C_{2-4}$ alkenyl" indicates that there are two to four carbon atoms in the alkenyl chain, i.e., the alkenyl chain is selected from ethenyl; propen-1-yl; propen-2-yl; propen-3-yl; buten-1-yl; buten-2-yl; buten-3-yl; buten-4-yl; 1-methyl-propen-1-yl; 2-methyl-propen-1-yl; 1-ethyl-ethen-1-yl; 2-methyl-propen-3-yl; buta-1,3-dienyl; buta-1,2,-dienyl and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain comprising one or more triple bonds. Although the present definition covers the occurrence of the term "alkynyl" where no numerical range is designated, the alkynyl group may have at least 2, 3, 4, 5, 6, 7, 8, 9, 10, 11, 12, 13, 14, 15, 16, 17, 18, 19, or 20 carbon atoms, or any number in between. For example, the alkynyl group may be designated as "$C_{2-4}$ alkynyl" "$C_{2-10}$ alkynyl" "$C_{2-20}$ alkynyl" or similar designations. By way of example only, "$C_{2-4}$ alkynyl" indicates that there are two to four carbon atoms in the alkynyl chain, e.g., the alkynyl chain is selected from ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "cycloalkyl" means a fully saturated carbocyclic ring radical or ring system. Examples include, but are not limited to, cyclopropyl, cyclobutyl, cyclopentyl, and cyclohexyl.

As used herein, "aryl" refers to a carbocyclic (all carbon) monocyclic or multicyclic aromatic ring system (including fused ring systems where two carbocyclic rings share a chemical bond). The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, phenyl, benzyl, α-naphthyl, β-naphthyl, biphenyl, anthryl, tetrahydronaphthyl, fluorenyl, indanyl, biphenylenyl, and acenaphthenyl. Preferred aryl groups are phenyl and naphthyl.

As used herein, "heteroaryl" refers to an aromatic ring or ring system (i.e., two or more fused rings that share two adjacent atoms) that comprise(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, "haloalkyl" refers to an alkyl group, in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, a "substituted" group may be substituted with one or more group(s) individually and independently selected from alkyl, alkenyl, alkynyl, cycloalkyl, cycloalkenyl, cycloalkynyl, benzyl, substituted benzyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiol, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

As used herein, "halogen" refers to an atom of fluorine, chlorine, bromine or iodine.

As used herein, "homocyclic ring" refers to cycloalkyl or aryl.

As used herein, "heterocyclic ring" refers to a ring, which may contain 1 to 4 hetero-atoms selected from among nitrogen, oxygen, sulfur and other atoms in addition to carbon atoms.

As used herein, the term "alcohol" is art-recognized and refers to any substance having an OH group attached to a carbon. In certain embodiments, the alcohol is a primary alcohol, a secondary alcohol, or a tertiary alcohol. In some embodiments, the alcohol is a monohydric alcohol or a polyhydric alcohol. In certain embodiments, the alcohol is a diol, triol, tetraol, pentol, or hexol. In one embodiment, the alcohol is an aliphatic alcohol including saturated aliphatic or unsaturated aliphatic alcohol. In some embodiments, the alcohol is an allylic, homoallylic, doubly allylic, doubly homoallylic, propargylic, homopropargylic, doubly propargylic, doubly homopropargylic, benzylic, homobenzylic, doubly benzylic, or doubly homobenzylic alcohol. In certain embodiments, the alcohol is a glycol, a glycerol, an erythritol, a xylitol, a mannitol, an inositol, a menthol or a naturally or non-naturally occurring sugar. In other embodiments, the alcohol is a cycloalkanol, a phenol or other aryl alcohol, or a heteroaryl alcohol. Any of the aforementioned alcohols may be optionally substituted with one or more halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, and cyano groups. Examples include, but are not limited to, methanol, ethanol, isopropyl alcohol, butyl alcohol, isobutyl alcohol, t-butanol, pentanol, pentan-2-ol, pentan-3-ol, hexanol, heptanol, octanol, cyclopentanol, cyclohexanol, benzyl alcohol, 2-phenylethan-1-ol, 2-phenylpropan-2-ol, 5-phenyl-pent-1-ol, 2,2,2-trifluoroethan-1-ol, 2-methoxyethan-1-ol and the like.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system.

For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

Dinuclear Copper Catalyst

In one embodiment, the subject invention provides a dinuclear copper catalyst that performs oxidation reactions—either oxygenation or dehydrogenation reactions—of various substrates containing C—H bonds, e.g., hydrocarbons. In one embodiment, the dinuclear copper catalyst comprises a dinuclear copper complex, i.e., dinuclear Cu(I)/Cu(II) complex, comprising a copper-containing compound having a bi-copper center joined by one or more bidentate or multidentate ligands.

The dinuclear Cu(I)/Cu(II) complex can cycle between the resting $Cu(I)_2$ state, i.e., the dinuclear Cu(I) complex, and the catalytically active or oxidized $Cu(II)_2$ form, i.e., the dinuclear Cu(II) complex. The dinuclear Cu(I) complexes convert to the dinuclear Cu(II) complex upon exposure to, for example, atmospheric oxygen, and peroxides. For example, in the presence of $O_2$, the dinuclear Cu(I) complexes is oxidized to the dinuclear Cu(II) complex comprising a μ-OH at the bi-copper center, wherein the μ-OH can form a hydrogen bond with a counterion, such as an ionic ligand, stabilizing the dinuclear Cu(II) complex. The dinuclear Cu(II) complex returns to the resting $Cu(I)_2$ state, i.e., the dinuclear Cu(I) complex upon reacting with a substrate comprising at least one reactive C—H bonds, e.g., hydrocarbons, by either dehydrogenating the substrate with formation of $H_2O$, or oxygenating the substrate by adding its O-atom to the substrate.

In one embodiment, the dinuclear copper complex comprises a dinuclear copper compound and a stabilizing ligand, wherein when the dinuclear copper compound is at the resting state, i.e., being the dinuclear Cu(I) species, the stabilizing ligand stays neutral; and when the dinuclear copper compound is at the oxidized state, i.e., being the dinuclear Cu(II) species, the stabilizing ligand is ionic and can form a hydrogen bond with a μ-OH at the bi-copper center of the dinuclear Cu(II) species. The stabilization of the dinuclear Cu(II) species by a hydrogen-bonded stabilizing ligand ion is a key factor of the catalytic performance of the dinuclear copper catalyst.

In one embodiment, the dinuclear Cu(I) compound/species/complex has a general structure of the formula (A):

wherein represents a peripheral chelating ligand substitution, preferably, is and wherein $R_1$, $R_3$, $R_4$, $R_5$, $R_6$, $R_3'$, $R_4'$, $R_5'$, $R_6'$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, —COOH, —$NO_2$, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, acyl, carboxyalkyl, halogen, amino, substituted amino, hydroxyl, hydroxylalkyl, and substituted hydroxylalkyl.

In a further embodiment, $R_1$, $R_3$, $R_4$, $R_5$, $R_6$, $R_3'$, $R_4'$, $R_5'$, $R_6'$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, —COOH, —$NO_2$, alkyl, substituted alkyl, alkenyl, substituted alkenyl, alkoxy, substituted alkoxy, acyl, carboxyalkyl, halogen, amino, substituted amino, hydroxyl, and hydroxylalkyl.

In a preferred embodiment, $R_1$, $R_3$, $R_4$, $R_5$, $R_6$, $R_3'$, $R_4'$, $R_5'$, $R_6'$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, —$NO_2$, alkyl, alkoxy, halogen, amino, and hydroxyl.

In specific embodiments, at least one of $R_1$, $R_3$, $R_4$, $R_5$, $R_6$, $R_3'$, $R_4'$, $R_5'$, $R_6'$, $R_2''$, $R_3''$, $R_4''$, $R_5''$, $R_6''$, $R_2'''$, $R_3'''$, $R_4'''$, $R_5'''$, and $R_6'''$ is —$NO_2$.

In a specific embodiment, $R_3$, $R_4$, $R_5$, $R_6$, $R_3'$, $R_4'$, $R_5'$, and $R_6'$ are each independently selected from the group consisting of hydrogen, F, Cl, Br, I, Me, $CF_3$, OMe, and tert-Bu.

In a specific embodiment, the dinuclear Cu(I) compound/species/complex has a structure of:

wherein is and wherein $R_3$, $R_4$, $R_5$, $R_6$, $R_3'$, $R_4'$, $R_5'$, and $R_6'$ are each independently selected from the group consisting of hydrogen, F, Cl, Br, I, Me, $CF_3$, OMe, and tert-Bu.

In specific embodiments, $R_3$, $R_4$, $R_5$, $R_3'$, $R_4'$, and $R_5'$, are each hydrogen; and $R_6$, and $R_6'$ are each independently selected from the group consisting of F, Cl, Br, I, Me, $CF_3$, OMe, and tert-Bu.

In specific embodiments, $R_3$, $R_4$, $R_6$, $R_3'$, $R_4'$, and $R_6'$, are each hydrogen; and $R_5$, and $R_5'$ are each independently selected from the group consisting of F, Cl, Br, I, Me, $CF_3$, OMe, and tert-Bu.

In specific embodiments, $R_3$, $R_5$, $R_6$, $R_3'$, $R_5'$ and $R_6'$ are each hydrogen; and $R_4$, and $R_4'$ are each independently selected from the group consisting of F, Cl, Br, I, Me, $CF_3$, OMe, and tert-Bu.

In specific embodiments, $R_4$, $R_5$, $R_6$, $R_4'$, $R_5'$ and $R_6'$ are each hydrogen; and $R_3$ and $R_3'$ are each independently selected from the group consisting of F, Cl, Br, I, Me, $CF_3$, OMe, and tert-Bu.

In specific embodiments, $R_3$, $R_4$, $R_5$, $R_6$, $R_4'$, $R_5'$ and $R_6'$ are each hydrogen; and $R_3'$ is selected from the group consisting of F, Cl, Br, I, Me, $CF_3$, OMe, and tert-Bu.

In specific embodiments, $R_3$, $R_4$, $R_5$, $R_6$, $R_3'$, $R_5'$ and $R_6'$ are each hydrogen; and $R_4'$ is selected from the group consisting of F, Cl, Br, I, Me, $CF_3$, OMe, and tert-Bu.

In specific embodiments, $R_3$, $R_4$, $R_5$, $R_6$, $R_3'$, $R_4'$, and $R_6'$ are each hydrogen; and $R_5'$ is selected from the group consisting of F, Cl, Br, I, Me, $CF_3$, OMe, and tert-Bu.

In specific embodiments, $R_3$, $R_4$, $R_5$, $R_6$, $R_3'$, $R_4'$, and $R_5'$ are each hydrogen; and $R_6'$ is selected from the group consisting of F, Cl, Br, I, Me, $CF_3$, OMe, and tert-Bu.

In a specific embodiment is

In a specific embodiment, $R_1$, $R_2''$, $R_4''$, $R_2'''$, $R_6''$, $R_4'''$, and $R_6'''$ cannot all be —$NO_2$ at the same time.

In one embodiment, the dinuclear Cu(II) compound/species/complex has a general structure of the formula (B):

wherein represents a peripheral chelating ligand substitution, preferably, is and wherein $R_1$, $R_3$, $R_4$, $R_5$, $R_6$, $R_3'$, $R_4'$, $R_5'$, $R_6'$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, —COOOH, —$NO_2$, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, acyl, carboxyalkyl, halogen, amino, substituted amino, hydroxyl, hydroxyalkyl, and substituted hydroxyalkyl.

In a further embodiment, $R_1$, $R_3$, $R_4$, $R_5$, $R_6$, $R_3'$, $R_4'$, $R_5'$, $R_6'$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, —COOH, —$NO_2$, alkyl, substituted alkyl, alkenyl, substituted alkenyl, alkoxy, substituted alkoxy, acyl, carboxyalkyl, halogen, amino, substituted amino, hydroxyl, and hydroxyalkyl.

In a preferred embodiment, $R_1$, $R_3$, $R_4$, $R_5$, $R_6$, $R_3'$, $R_4'$, $R_5'$, $R_6'$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, —$NO_2$, alkyl, alkoxy, halogen, amino, and hydroxyl.

In specific embodiments, at least one of $R_1$, $R_3$, $R_4$, $R_5$, $R_6$, $R_3'$, $R_4'$, $R_5'$, $R_6'$, $R_2''$, $R_3''$, $R_4''$, $R_5''$, $R_6''$, $R_2'''$, $R_3'''$, $R_4'''$, $R_5'''$, and $R_6'''$ is —$NO_2$.

In a specific embodiment, $R_3$, $R_4$, $R_5$, $R_6$, $R_3'$, $R_4'$, $R_5'$, and $R_6'$ are each independently selected from the group consisting of hydrogen, F, Cl, Br, I, Me, $CF_3$, OMe, and tert-Bu.

In a specific embodiment, the dinuclear Cu(II) compound/species/complex has a structure of:

wherein is and wherein $R_3$, $R_4$, $R_5$, $R_6$, $R_3'$, $R_4'$, $R_5'$, and $R_6'$ are each independently selected from the group consisting of hydrogen, F, Cl, Br, I, Me, $CF_3$, OMe, and tert-Bu.

In specific embodiments, $R_3$, $R_4$, $R_5$, $R_3'$, $R_4'$, and $R_5'$, are each hydrogen; and $R_6$, and $R_6'$ are each independently selected from the group consisting of F, Cl, Br, I, Me, $CF_3$, OMe, and tert-Bu.

In specific embodiments, $R_3$, $R_4$, $R_6$, $R_3'$, $R_4'$, and $R_6'$, are each hydrogen; and $R_5$, and $R_5'$ are each independently selected from the group consisting of F, Cl, Br, I, Me, $CF_3$, OMe, and tert-Bu.

In specific embodiments, $R_3$, $R_5$, $R_6$, $R_3'$, $R_5'$ and $R_6'$ are each hydrogen; and $R_4$, and $R_4'$ are each independently selected from the group consisting of F, Cl, Br, I, Me, $CF_3$, OMe, and tert-Bu.

In specific embodiments, $R_4$, $R_5$, $R_6$, $R_4'$, $R_5'$ and $R_6'$ are each hydrogen; and $R_3$ and $R_3'$ are each independently selected from the group consisting of F, Cl, Br, I, Me, $CF_3$, OMe, and tert-Bu.

In specific embodiments, $R_3$, $R_4$, $R_5$, $R_6$, $R_4'$, $R_5'$ and $R_6'$ are each hydrogen; and $R_3'$ is selected from the group consisting of F, Cl, Br, I, Me, $CF_3$, OMe, and tert-Bu.

In specific embodiments, $R_3$, $R_4$, $R_5$, $R_6$, $R_3'$, $R_5'$ and $R_6'$ are each hydrogen; and $R_4'$ is selected from the group consisting of F, Cl, Br, I, Me, $CF_3$, OMe, and tert-Bu.

In specific embodiments, $R_3$, $R_4$, $R_5$, $R_6$, $R_3'$, $R_4'$, and $R_6'$ are each hydrogen; and $R_5'$ is selected from the group consisting of F, Cl, Br, I, Me, $CF_3$, OMe, and tert-Bu.

In specific embodiments, $R_3$, $R_4$, $R_5$, $R_6$, $R_3'$, $R_4'$, and $R_5'$ are each hydrogen; and $R_6'$ is selected from the group consisting of F, Cl, Br, I, Me, $CF_3$, OMe, and tert-Bu.

In a specific embodiment, is

In a specific embodiment, $R_1$, $R_2''$, $R_4''$, $R_2'''$, $R_6''$, $R_4'''$, and $R_6'''$ cannot all be $-NO_2$ at the same time.

In one embodiment, the dinuclear copper catalyst comprises a stabilizing free ligand as counterion, whose ionic form has a general structure of that can form a hydrogen bond with the μ-OH of the dinuclear Cu(II) complex, while the neutral form of the free ligand has a general structure of wherein $R_1$, $R_2''$, $R_3''$, $R_4''$, $R_5''$, $R_6''$, $R_2'''$, $R_3'$, $R_4'''$, $R_5'''$, and $R_6'''$ are each independently selected from the group consisting of hydrogen, —COOH, —$NO_2$, alkyl, substituted alkyl, aryl, substituted aryl, heteroalkyl, substituted heteroalkyl, heteroaryl, substituted heteroaryl, cycloalkyl, substituted cycloalkyl, heterocycloalkyl, substituted heterocycloalkyl, cycloalkenyl, substituted cycloalkenyl, alkenyl, substituted alkenyl, alkynyl, alkoxy, substituted alkoxy, acyl, carboxyalkyl, halogen, amino, substituted amino, hydroxyl, hydroxylalkyl, and substituted hydroxylalkyl.

In one embodiment, the dinuclear copper complex comprises a stabilizing ligand or counter ion that can be the same or different from the bidentate or multidentate ligand of the dinuclear copper compound.

In a further embodiment, $R_1$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, —COOH, —$NO_2$, alkyl, substituted alkyl, alkenyl, substituted alkenyl, alkoxy, substituted alkoxy, acyl, carboxyalkyl, halogen, amino, substituted amino, hydroxyl, and hydroxylalkyl.

In a preferred embodiment, $R_1$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, —$NO_2$, alkyl, alkoxy, halogen, amino, and hydroxyl. In a specific embodiment, at least one of $R_1$, $R_2''$, $R_3''$, $R_4''$, $R_5''$, $R_6''$, $R_2'''$, $R_3'''$, $R_4'''$, $R_5'''$, and $R_6'''$ is —$NO_2$. In a specific embodiment, $R_1$, $R_2''$, $R_4''$, $R_2'''$, and $R_4'''$ cannot all be —$NO_2$ at the same time.

In a specific embodiment, the stabilizing ligand comprises a sterically bulk poly-nitro pyrazolato ligand, for example, a pyrazolate, e.g., 3,5-bis(2,4-dinitrophenyl)-4-nitro-pyrazolate (pnpz-). Preferably, the stabilizing agent has a structure of while the ionic form of the stabilizing ligand has a general structure of In a specific embodiment, the copper catalyst is [{($\eta^2$-2,2'-bipy)Cu$^{II}$($\mu$-pnpz)}$_2$($\mu$-OH)](pnpz).

In a specific embodiment, the copper catalyst cannot be [{($\eta^2$-2,2'-bipy)Cu$^{II}$($\mu$-pnpz)}$_2$($\mu$-OH)](pnpz).

In one embodiment, the interconversion of the dinuclear copper species and the catalytic reaction may be represented, for example, by Scheme 1:

wherein L is the stabilizing ligand, and - - - represents the hydrogen bond between $\mu$-OH and the stabilizing ligand.

The advantages of the dinuclear copper catalyst include: 1) it comprises earth abundant metal copper, which is cost-effective and sustainable; 2) atmospheric oxygen can be used as oxidant to oxidize the Cu(I)-Cu(I) resting state of the complex to a Cu(II)—OH—Cu(II) species; 3) ligands of the complex are readily available; 4) the properties of the catalyst can be tuned via judicious peripheral ligand substitution and the peripheral ligand substitution can produce catalysts tailored to specific applications; and 5) the catalyst is easy to prepare under ambient conditions; no inert atmosphere, and special instrumentations are required.

In one embodiment, the subject invention provides a method for synthesizing the dinuclear copper catalyst, the method comprising mixing a Cu(II) starting material, and one or more didentate or multidentate ligands in a solvent. In a preferred embodiment, the Cu(II) starting material comprises Cu(OH)$_2$. In a specific embodiment, the Cu(II) starting material is, for example, Cu(OH)$_2$. In a preferred embodiment, the method comprises mixing a Cu(II) starting material with one or more didentate ligands, for example, 2,2'-bipyridine (bipy) and 3,5-bis(2,4-dinitrophenyl)-4-nitro-pyrazole (pentanitropyrazole, pnpzH).

In one embodiment, the subject invention also provides compositions comprising the dinuclear copper catalyst, or dinuclear copper complexes. In a specific embodiment, the dinuclear copper catalyst comprises a mixture of the dinuclear Cu(I) complex and the dinuclear Cu(II) complex. In a specific embodiment, the dinuclear copper catalyst comprises pure dinuclear Cu(II) complex. In one embodiment, the composition further comprises a carrier, or solvent.

Examples of the carrier include, but not limited to, aqueous vehicles, water-miscible vehicles, non-aqueous vehicles, stabilizers, solubility enhancers, isotonic agents, buffering agents, suspending and dispersing agents, wetting or emulsifying agents, complexing agents, sequestering or chelating agents, cryoprotectants, lyoprotectants, thickening agents, pH adjusting agents, and inert gases. Other suitable excipients or carriers include, but are not limited to, dextran, glucose, maltose, sorbitol, xylitol, fructose, sucrose, and trehalose.

Examples of the solvent include, but are not limited to, butyl acetate, tert-butylmethyl ether, dimethyl sulfoxide, ethyl acetate, ethyl formate, heptane, isobutyl acetate, isopropyl acetate, methyl acetate, methylethyl ketone, methylisobutyl ketone, pentane, hexane, propyl acetate, MeCN, EtCN, PrCN, and supercritical CO$_2$. In a specific embodiment, the solvent comprises MeCN.

Method of Use

In one embodiment, the subject invention provides a method for using the catalyst of the subject invention to oxidize C—H bonds to form C—OH and/or C=C bonds, to oxidize C—OH bonds to C=O bonds, and/or to oxidize and cleave C—C bonds in a substrate. The methods involve the combination of a substrate comprising one or more of reactive C—H, C—OH, and/or C—C bonds, and a catalyst of the subject invention under, for example, ambient conditions. The methods are useful for the formation of, for example, alkenes, alcohols, aldehyde, ketones and/or aromatic rings. Advantageously, the methods of the subject invention minimize reaction steps, the handling of oxidized intermediates, and environmental impact.

In certain embodiments, the substrate is a DHA, toluene, 2,2,4-trimethylpentane, methylcyclohexane, methane, cyclopropane, cyclobutane, cyclopentane, cyclohexane, indane, 2-oxoindane, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactone, lactam, azetidinone, pyrrolidinone, sultam, or sultone; and the substrate is optionally substituted with halogens, alkyls, alkenyls, alkynyls, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, fluoroalkyls, trifluoromethyl, or cyano.

In certain embodiments, the methods for synthesizing alkenes and/or alcohols use, for example, hydrocarbons as substrates via copper-mediated C—H oxygenation to form C—OH or via copper-mediated C—H dehydrogenation to form C=C.

In one embodiment, the methods for synthesizing aldehyde and/or ketones uses, for example, alcohols, as substrates via copper-mediated dehydrogenation of C—OH to form a C=O and/or —CHO group.

In one embodiment, the subject invention provides a method of copper-mediated oxidization and cleavage of one or more C—C bonds of a substrate. Preferably, the C—C bond is the one adjacent to a C=O group, i.e., C—C=O.

In one embodiment, the subject invention provides a method for catalyzing or oxidizing a substrate (e.g., hydrocarbon) comprising at least one reactive C—H bond, the method comprising contacting the substrate (e.g., hydrocarbon) with the dinuclear copper catalyst of the subject invention, thereby forming a oxidized product comprising at least one C—OH by adding the O atom of the dinuclear Cu(II) species to C—H bonds, and/or at least one C=C bond by dehydrogenating from the C—H bonds.

In one embodiment, the subject invention provides a method for catalyzing or oxidizing a substrate comprising at least a reactive C—OH bond, the method comprising contacting, combining, and/or mixing the substrate with the dinuclear copper catalyst of the subject invention, thereby forming a oxidized product comprising at least one C=O bond.

In one embodiment, the subject invention provides a method for catalyzing or oxidizing an alcohol, the method comprising contacting, combining, and/or mixing the alcohol with the dinuclear copper catalyst of the subject invention.

In one embodiment, the subject invention provides a method for producing an alcohol, the method comprising contacting, combining, and/or mixing a substrate (e.g., hydrocarbon) with the dinuclear copper catalyst of the subject invention, the substrate (e.g., hydrocarbon) comprising at least one reactive C—H bond.

In one embodiment, the subject invention provides a method for producing an alkene, the method comprising contacting, combining, and/or mixing a substrate (e.g., hydrocarbon) with the dinuclear copper catalyst of the subject invention, the substrate (e.g., hydrocarbon) comprising at least one reactive C—H bond.

In one embodiment, the subject invention provides a method for producing an aromatic ring, the method comprising contacting, combining, and/or mixing a substrate (e.g., hydrocarbon) with the dinuclear copper catalyst of the subject invention, the substrate (e.g., hydrocarbon) comprising at least one reactive C—H bond. Preferably, the substrate is a hydrocarbon comprising one or more 5, and/or 6 membered rings.

In one embodiment, the subject invention provides a method for producing an aldehyde, the method comprising contacting, combining, and/or mixing a substrate (e.g., hydrocarbon) with the dinuclear copper catalyst of the subject invention, the substrate (e.g., hydrocarbon) comprising at least one reactive C—H bond. In certain embodiments, producing an aldehyde may comprise a series of catalytic reactions including, for example, a step of producing an alcohol from the reaction between the substrate (e.g., hydrocarbon) and the dinuclear copper catalyst, and a step of producing the aldehyde from the reaction between the alcohol and the dinuclear copper catalyst.

In one embodiment, the subject invention provides a method for producing a ketone, the method comprising contacting a substrate (e.g., hydrocarbon) with the dinuclear copper catalyst of the subject invention, the substrate (e.g., hydrocarbon) comprising at least one reactive C—H bond. In certain embodiments, producing a ketone may comprise a series of catalytic reactions including, for example, a step of producing an alcohol from the reaction between the substrate (e.g., hydrocarbon) and the dinuclear copper catalyst, and a step of producing the ketone from the reaction between the alcohol and the dinuclear copper catalyst.

In certain embodiments, the subject invention provides methods for oxidizing a substrate by using the dinuclear copper catalyst of the subject invention, the methods comprising one or more of the following oxidization steps:

1) oxygenating one or more C—H bonds of the substrate, e.g., hydrocarbon, to form one or more C—OH bonds;

2) dehydrogenating one or more C—H bonds of the substrate to form one or more C=C bonds, preferably, the substrate having one or more ring structures, more preferably, one or more C—H bonds being in 5- and/or 6-membered rings;

3) oxidizing one or more C—OH bonds of the substrate, e.g., hydrocarbon, to form one or more C=O bonds; and 4) oxidizing and cleaving one or more C—C bonds of the substrate to break the bonding of such two carbons, preferably, the C—C bond is adjacent to a C=O group. For example, the substrate comprises one or more C—C=O groups.

In one embodiment, the substrate has a C—H bond energy of at least 300 kJ/mol, at least 310 kJ/mol, at least 320 kJ/mol, at least 330 kJ/mol, at least 340 kJ/mol, at least 350 kJ/mol, at least 360 kJ/mol, at least 370 kJ/mol, at least 380 kJ/mol, at least 390 kJ/mol, at least 400 kJ/mol, at least 410 kJ/mol, at least 420 kJ/mol, at least 430 kJ/mol, at least 440 kJ/mol, or any in between. In some embodiments, the substrate has a C—H bond energy of, for example, at least 364 kJ/mol, at least 365 kJ/mol, at least 384 kJ/mol, at least 418 kJ/mol, or at least 439 kJ/mol.

In one embodiment, the catalytic reaction occurs with atmospheric oxygen. Preferably, the catalytic reaction occurs in the presence of pure $O_2$. The catalytic reaction performs better with pure $O_2$ than with ambient air (atmospheric oxygen).

In one embodiment, the methods of the subject invention comprise a step of identifying or detecting the product including intermediate product and/or final product of the catalytic reaction by methods known in the art, for example, GC-MS, UV-Vis, NMR and/or X-ray crystallography.

In one embodiment, the method of the subject invention may further comprise a step of determining whether the oxygen is limited and the catalytic reaction is terminated, wherein a color change in the mixture of the substrate and the dinuclear copper catalyst from green to red/orange/ brown is indicative that the oxygen is limited and the catalytic reaction is terminated.

In one embodiment, the subject invention also provides a method for recovering the resting dinuclear copper catalyst, the method comprising mixing the dinuclear copper catalyst with a substrate in a closed container, and recovering the dinuclear copper catalyst at the resting state when a color change in the mixture from green to red/orange/brown occurs.

In one embodiment, the reaction in the methods of the subject invention takes place in a solvent. Examples of the solvent include, but are not limited to, acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methyl-isobutyl ketone, 2-methyl-1-propanol, pentane, 1-pentanol, 1-propanol, 2-propanol and propyl acetate. In a specific embodiment, the solvent comprises MeCN.

In one embodiment, the reaction in the methods of the subject invention may run at a temperature ranging from about 4° C. to about 100° C., from about 10° C. to about 90° C., from about 20° C. to about 80° C., from about 20° C. to about 70° C., from about 20° C. to about 60° C., from about 20° C. to about 50° C., from about 20° C. to about 40° C., from about 20° C. to about 30° C., from about 30° C. to about 70° C., from about 30° C. to about 50° C., from about 40° C. to about 70° C., from about 40° C. to about 80° C., from about 50° C. to about 90° C., or from about 50° C. to about 100° C. Preferably, the reaction in the methods of the subject invention may run at room temperature.

The catalyst can be used in a wide range of amount in the reaction according to the subject invention. For example, the catalyst may be present in less than about 90 mol %, about 85 mol %, about 80 mol %, about 75 mol %, about 70 mol %, about 65 mol %, about 60 mol %, about 55 mol %, about 50 mol %, about 45 mol %, about 40 mol %, about 35 mol %, about 30 mol %, about 25 mol %, about 20 mol %, about 15 mol %, about 10 mol %, about 5 mol %, or about 1 mol %, relative to the substrate.

In one embodiment, the catalyst and the substrate in a reaction according to the subject invention may be loaded at a molar ratio of, for example, from 1:1 to 1:500, from 1:1 to 1:400, from 1:1 to 1:300, from 1:1 to 1:250, from 1:1 to 1:200, from 1:1 to 1:150, from 1:1 to 1:100, from 1:1 to 1:90, from 1:1 to 1:80, from 1:1 to 1:70, from 1:1 to 1:60, from 1:1 to 1:50, from 1:1 to 1:40, from 1:1 to 1:30, from 1:1 to 1:20, from 1:1 to 1:10, or from 1:1 to 1:5.

In one embodiment, the reaction of the subject invention has a product yield of at least about 5%, at least about 10%, at least about 15%, at least about 20%, at least about 25%, at least about 30%, at least about 35%, at least about 40%, at least about 45, at least about 50%, at least about 55%, at least about 60%, at least about 65%, at least about 70%, at least about 75%, at least about 80%, at least about 85%, at least about 90%, at least about 95%, at least about 99%, or at least about 99.5%. In a preferred embodiment, the reaction of the subject invention has a product yield of 99.9% or 100%.

When ranges are used herein, such as for dose ranges, combinations and subcombinations of ranges (e.g., subranges within the disclosed range), specific embodiments therein are intended to be explicitly included.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

EXAMPLES

The copper complexes described herein can be prepared under ambient conditions open to the atmosphere. The catalyst is easily synthesized in good yield from a commercially available Cu(II) starting material, 2,2'-bipyridine (bipy) and 3,5-bis(2,4-dinitrophenyl)-4-nitro-pyrazole (pentanitropyrazole, pnpzH). The $Cu(II)_2(\mu\text{-OH})$ product, $[\{(\eta^2\text{-}2,2'\text{-bipy})Cu(II)(\mu\text{-pnpz})\}_2(\mu\text{-OH})](pnpz)$, can be characterized by elemental analysis, mass spectroscopy and single crystal X-ray structure determination. The green crystalline solid cation crystallizes with a pnpz anion H-bonded to the $\mu$-OH group.

Reaction of $Cu(OH)_2$, pnpzH and 2,2'-bipy in acetonitrile yields the $[\{(\eta^2\text{-}2,2'\text{-bipy})Cu(II)(\mu\text{-pnpz})\}_2(\mu\text{-OH})](pnpz)$ complex ($Cu(II)_2$), as follows.

$[\{(\eta^2\text{-}2,2'\text{-bipy})Cu(II)(\mu\text{-pnpz})\}_2(\mu\text{-OH})](pnpz)$: 25.6 mg (0.262 mmol) $Cu(OH)_2$ and 200 mg (0.397 mmol) pnpzH were stirred in 5 mL $CH_3CN$ until all solids were dissolved. To the resulting light blue solution, was added 41 mg (0.262 mmol) 2,2'-bipy, turning gradually the solution color from light green to deep green over a period of 2 h. The green reaction mixture was filtered through Celite and was set to crystallize by slow diethylether vapor diffusion, resulting in single crystals appropriate for X-ray diffraction analysis; Yield, 288 mg (62%). For $C_{65}H_{35}N_{25}O_{31}Cu_2$: Calc./Found %, C, 43.63/43.47; H, 1.97/1.89; N, 19.57/19.20. UV-Vis (nm, $CH_3CN$): 247, 304, 316 (sh), 380.

X-ray structural determination, $Cu^{II}_2$.x Solvent: $C_{65}H_{35}Cu_2N_{25}O_{31}$, M=1789.26, triclinic P-1, a=16.480(6) Å, b=16.668(6) Å, c=22.481(8) Å, α=76.090(9)°, β=74.621(9)°, γ=69.582(9)°, V=5505(3) Å$^3$, Z=2, d=1.090 g/cm$^3$, $R_1$=5.34% and GoF=1.046 for 1124 parameters refined with 12559 observed reflections.

Figure 1:
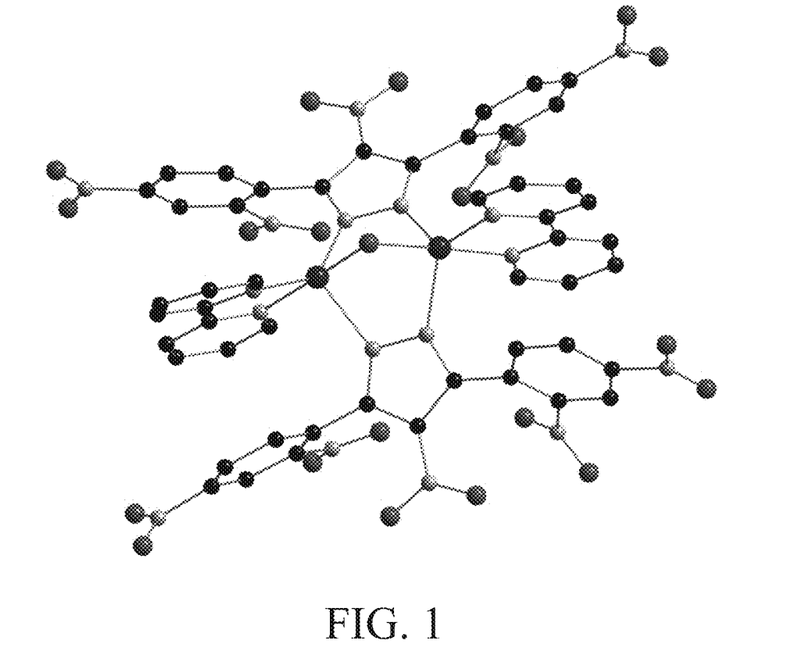
FIG. 1 shows the ball-and-stick diagram of $Cu(II)_2(\mu\text{-OH})$ $(\mu\text{-pnpz})_2(\eta^2\text{-2,2'-bipy})_2$. The hydrogen atoms and pentanitropyrazole (pnpz⁻) anion are not shown for clarity. Color code: Cu, blue; O, red; N, light blue; C, black.

The crystal structure of $[\{(\eta^2\text{-}2,2'\text{-bipy})Cu(II)(\mu\text{-pnpz})\}_2(\mu\text{-OH})](pnpz)$ consists of a dinuclear copper molecule—Cu . . . Cu, 3.003 Å—held together by two bridging pyrazolato ligands—Cu—N, 2.040-2.161 Å—and one bridging hydroxide—Cu—O, 1.912 and 1.931 Å (FIG. 1).

Example 1—Dicopper Complex Catalyzes Dihydroanthracene to Anthracene

Figure 2:
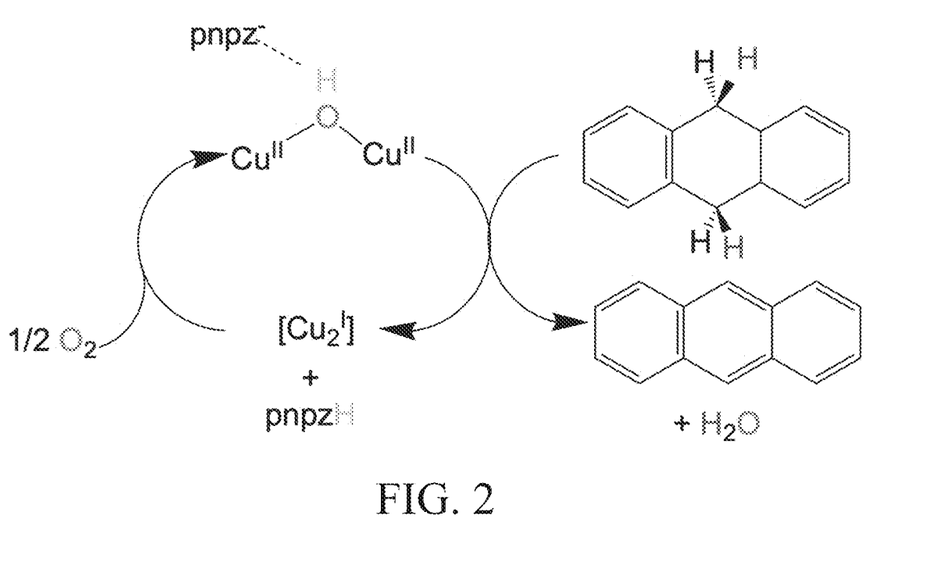
FIG. 2 shows the scheme of $Cu(II)_2(\mu\text{-OH})$ catalyzing dihydroanthracene to anthracene. A hydrogen bond is formed between the hydrogen of (μ-OH) and pnpz anion.

Atmospheric dioxygen ($O_2$) can oxidize $Cu(I)_2$ to $Cu(II)_2$, and the latter carries out oxidation reactions of hydrocarbon substrates, cycling between $Cu(I)_2$ and $Cu(II)_2$ complexes. The reaction of $Cu(II)_2(\mu\text{-OH})$ with dihydroanthracene (DHA) was investigated in MeCN. The result shows that $Cu(II)_2(\mu\text{-OH})$ can catalyze DHA by dehydrogenating it to anthracene (FIG. 2). DHA has a C—H bond energy of 326 kJ/mol. Under stoichiometric conditions, the reaction is easily followed spectroscopically, and also by visual inspection, because the green $Cu(II)_2(\mu\text{-OH})$ turns into the red $Cu(I)_2$, which was isolated and fully characterized. In a 1:100 molar ratio of $Cu(II)_2(\mu\text{-OH})$ to DHA reaction mixture, the reaction proceeds as long as it remains open to the atmosphere. When the reaction is sealed, the green solution turns gradually to brownish-orange and the reactions stops. Exposing this mixture again to the atmosphere, causes the catalysts to turn to its original green color and the oxidation of DHA restarts.

The role of the H-bonded pnpz anion, which modifies the secondary coordination sphere of the metal centers, is critical to the catalytic activity: it shuttles the proton necessary for the formation of the μ-OH group, in a similar manner to the stabilization of Cu—OH moieties in metalloproteins. The isolated $Cu(I)_2$ species, upon oxidation does not possess the catalytic activity.

Figure 3:
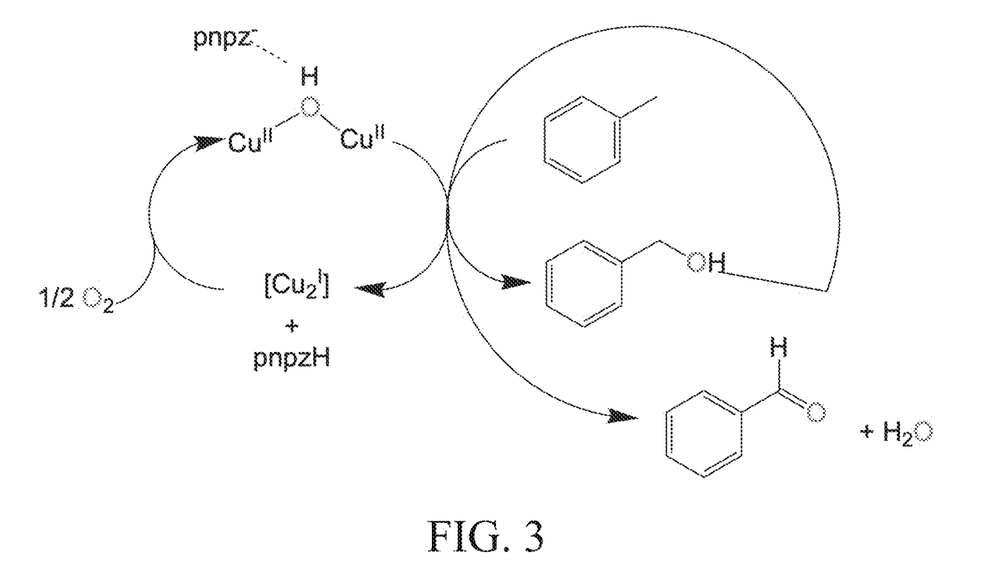
FIG. 3 shows the scheme of $Cu(II)_2(\mu\text{-OH})$ catalyzing toluene to benzyl alcohol and benzaldehyde. A hydrogen bond is formed between the hydrogen of (μ-OH) and pnpz⁻ anion.

Example 2—Dicopper Complex Catalyzes Toluene to Benzyl Alcohol and Benzaldehyde The catalytic oxidation of toluene (C—H bond energy, 364 kJ/mol) in MeCN was investigated. The result shows that $Cu(II)_2(\mu\text{-OH})$ can catalyze toluene by oxygenating (i.e., adding the O-atom of IA-OH to the substrate) it to benzyl alcohol (FIG. 3), which can further be catalyzed by $Cu(II)_2(\mu\text{-OH})$ to benzaldehyde. Thus, the catalytic reaction produces a mixture of benzyl alcohol and benzaldehyde, which can be identified by GC-MS.

Example 3—Dicopper Complex Catalyzes Cyclohexane to Cyclohexanone/Cyclohexanol The catalytic oxidation of cyclohexane (C—H bond energy, 418 kJ/mol) in MeCN produces a mixture of cyclohexanol, cyclohexanone and 1,6-hexanediol, which can be identified by GC-MS. When the reaction is carried out in tetrahydrofuran (thf; bond energy, 384 kJ/mol), 1,4-butyrolactone is also found among the reaction products.

Example 4—Dicopper Complex Catalyzes 2,2,4-trimethylpentane, Methylcyclohexane and Methane

Dicopper complex is used to catalyze hydrocarbons with a higher C—H bond energy, for example, 2,2,4-trimethylpentane (431 kJ/mol), methylcyclohexane (both 439 kJ/mol) and methane (439 kJ/mol).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

We claim:

1. A method for oxidizing or oxygenating a hydrocarbon comprising mixing a dinuclear copper catalyst with the hydrocarbon, wherein the dinuclear copper catalyst comprises a dinuclear Cu(II) complex and a stabilizing counter ion, the dinuclear Cu(II) complex having a general structure of formula (B):

Formula (B)

wherein $$\begin{pmatrix} N \\ N \end{pmatrix}$$

is

[structure showing bipyridine with $R^4$, $R^3$, $R^{3'}$, $R^{4'}$, $R^5$, $R^{5'}$, $R^6$, $R^{6'}$];

and wherein $R_1$, $R_3$, $R_4$, $R_5$, $R_6$, $R_3'$, $R_4'$, $R_5'$, $R_6'$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, $-NO_2$, $-OH$, alkyl, substituted alkyl, aryl, heteroalkyl, alkenyl, substituted alkenyl, alkoxy, substituted alkoxy, acyl, carboxyalkyl, halogen, and amino.

2. The method of claim 1, the hydrocarbon being selected from alkanes, alkenes, alkynes, and aromatics.

3. The method of claim 1, the hydrocarbon being selected from dihydroanthracene (DHA), toluene, 2,2,4-trimethylpentane, methylcyclohexane, methane, cyclopropane, cyclobutane, cyclopentane, and cyclohexane.

4. The method of claim 1, the dinuclear Cu(II) complex being reduced to a dinuclear Cu(I) complex upon catalyzing the oxidation or oxygenation of the hydrocarbon, the dinuclear Cu(I) complex having a general structure of formula (A):

Formula (A)

wherein is and wherein $R_1$, $R_3$, $R_4$, $R_5$, $R_6$, $R_3'$, $R_4'$, $R_5'$, $R_6'$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, —$NO_2$, —OH, alkyl, substituted alkyl, aryl, heteroalkyl, alkenyl, substituted alkenyl, alkoxy, substituted alkoxy, acyl, carboxyalkyl, halogen, and amino.

5. The method of claim 4, wherein $R_3$, $R_4$, $R_5$, $R_6$, $R_3'$, $R_4'$, $R_5'$, and $R_6'$ are each independently selected from the group consisting of hydrogen, F, Cl, Br, I, Me, $CF_3$, OMe, and tert-Bu.

6. The method of claim 4, the dinuclear Cu(I) complex having a structure of:

wherein is

.

7. The method of claim 1, wherein $R_3$, $R_4$, $R_5$, $R_6$, $R_3'$, $R_4'$, $R_5'$, and $R_6'$ are each independently selected from the group consisting of hydrogen, F, Cl, Br, I, Me, $CF_3$, OMe, and tert-Bu.

8. The method of claim 1, the dinuclear Cu(II) complex having a structure of:

wherein is

.

9. The method of claim 1, the stabilizing counter ion having a general structure of:

wherein $R_1$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, —$NO_2$, alkyl, substituted alkyl, alkoxy, halogen, amino, and hydroxyl.

10. The method of claim 1, the stabilizing counter ion having a general structure of 11. The method of claim 1, the dinuclear copper catalyst comprising and wherein is

.

12. The method of claim 1, mixing the dinuclear copper catalyst with the hydrocarbon occurring in ambient air or pure oxygen.

13. A method for forming an alcohol, an aldehyde, or an alkene from a hydrocarbon, the method comprising mixing the hydrocarbon with a dinuclear copper catalyst, wherein the dinuclear copper catalyst comprises a dinuclear Cu(II) complex and a stabilizing counter ion, the dinuclear Cu(II) complex having a general structure of formula (B):

Formula (B)

wherein is and wherein $R_1$, $R_3$, $R_4$, $R_5$, $R_6$, $R_3'$, $R_4'$, $R_5'$, $R_6'$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydro- gen, —NO₂, —OH, alkyl, substituted alkyl, aryl, heteroalkyl, alkenyl, substituted alkenyl, alkoxy, substituted alkoxy, acyl, carboxyalkyl, halogen, and amino.

14. The method of claim 13, the hydrocarbon being selected from alkanes, alkenes, alkynes, and aromatics.

15. The method of claim 13, the hydrocarbon being selected from DHA, toluene, 2,2,4-trimethylpentane, methylcyclohexane, methane, cyclopropane, cyclobutane, cyclopentane, and cyclohexane.

16. The method of claim 13, wherein $R_3$, $R_4$, $R_5$, $R_6$, $R_3'$, $R_4'$, $R_5'$, and $R_6'$ are each independently selected from the group consisting of hydrogen, F, Cl, Br, I, Me, $CF_3$, OMe, and tert-Bu.

17. The method of claim 13, the stabilizing counter ion having a general structure of:

wherein $R_1$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, —NO₂, alkyl, substituted alkyl, alkoxy, halogen, amino, and hydroxyl.

18. The method of claim 13, the dinuclear copper catalyst comprising and wherein is

19. A method for oxidizing or oxygenating a hydrocarbon comprising mixing a dinuclear copper catalyst with the hydrocarbon, wherein the dinuclear copper catalyst comprises a dinuclear copper compound and a stabilizing counter ion, and wherein the stabilizing counter ion having a general structure of:

wherein $R_1$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, —NO₂, alkyl, substituted alkyl, alkoxy, halogen, amino, and hydroxyl.

20. The method of claim 19, the dinuclear copper compound having a general structure of formula (B):

Formula (B)

wherein is $$\text{[structure: bipyridine with substituents } R^4, R^3, R^{3'}, R^{4'}, R^5, R^{5'}, R^6, R^{6'}\text{]}$$

and wherein $R_1$, $R_3$, $R_4$, $R_5$, $R_6$, $R_3'$, $R_4'$, $R_5'$, $R_6'$, $R_2''$, $R_3''$, $R_4''$, $R_5''$, $R_6''$, $R_2'''$, $R_3'''$, $R_4'''$, $R_5'''$, and $R_6'''$ are each independently selected from the group consisting of hydrogen, —$NO_2$, —OH, alkyl, substituted alkyl, aryl, heteroalkyl, alkenyl, substituted alkenyl, alkoxy, substituted alkoxy, acyl, carboxyalkyl, halogen, and amino.

* * * * *